United States Patent [19]

Gundersen

[11] Patent Number: 4,575,372

[45] Date of Patent: Mar. 11, 1986

[54] INTRAOCULAR LENS AND METHOD OF MANUFACTURE USING ULTRASONIC BONDING

[75] Inventor: Ivan Gundersen, Diamond Bar, Calif.

[73] Assignee: Iolab Corporation, Covina, Calif.

[21] Appl. No.: 506,576

[22] Filed: Jun. 22, 1983

[51] Int. Cl.⁴ .......................... A61F 2/16; B32B 31/16; B29C 53/00
[52] U.S. Cl. ...................................... 623/6; 156/73.1; 156/73.2; 156/158; 264/281
[58] Field of Search ...................... 156/73.1, 73.2, 158, 156/503; 264/281; 3/13, 1

[56] References Cited

U.S. PATENT DOCUMENTS

| 4,242,761 | 1/1981 | Chase et al. | 3/13 |
| 4,298,995 | 11/1981 | Poler | 3/13 |
| 4,480,340 | 11/1984 | Shepard | 3/13 |

OTHER PUBLICATIONS

"Ultrasonic Welding of Plastics" by N. A. Ol'shanskii, et al., *Welding Production*, Sep.–Dec. 1959, pp. 85–92.

Primary Examiner—Ronald L. Frinks
Attorney, Agent, or Firm—Donal B. Tobin

[57] ABSTRACT

An intraocular lens loop, with an eyelet formed on the loop, and a method of forming the eyelet employing ultrasound energy. There is also disclosed a special fixture for use in manufacturing the eyelet loop.

39 Claims, 21 Drawing Figures

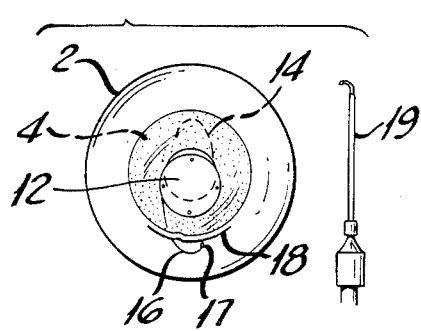
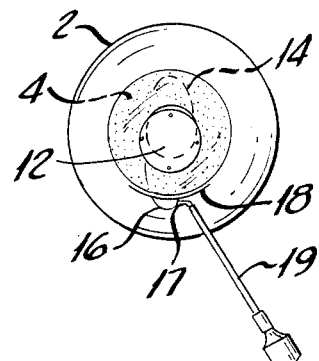
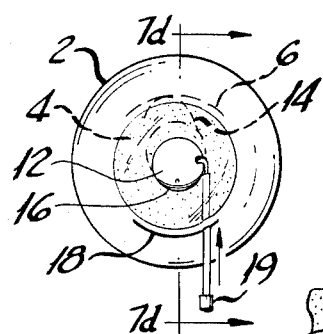
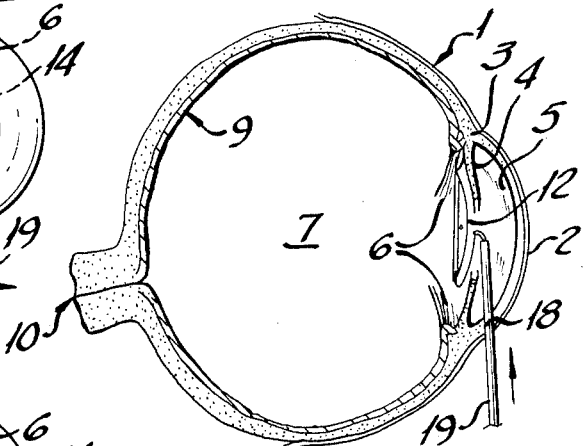
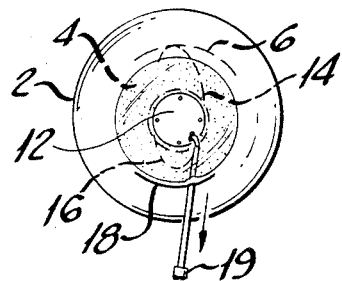
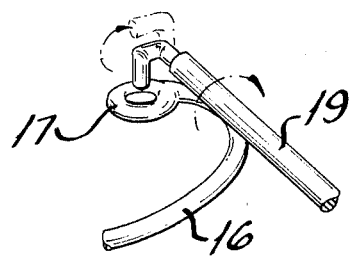
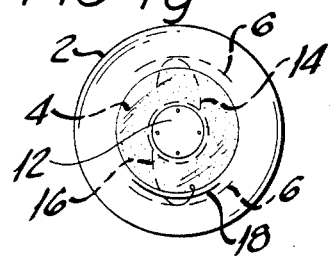

INTRAOCULAR LENS AND METHOD OF MANUFACTURE USING ULTRASONIC BONDING

The present invention relates to a loop-type support for an intraocular lens and more particularly a loop having an eyelet and to the method of manufacturing the eyelet using ultrasonic bonding.

It is now commonly accepted that the vision impairing disease known as cataracts can be alleviated by surgically replacing the natural lens of the eye with an artificial intraocular lens.

The anatomy of the eye, 1, is shown schematically in FIGS. 7a through 7f, particularly FIG. 7d. The cornea, 2, forms the first surface of the eye and connects with the ciliary muscle, 3, from which the iris, 4, extends. Iris, 4, divides the front portion of the eye into an anterior chamber, 5, between the iris 4 and cornea 2 and a posterior chamber, 6, behind the iris 4. The natural lens of the eye (not shown in FIG. 7) is supported in the posterior chamber, 6, by suspensory ligaments (also not shown). The remainder of the eye, 7, is called the vitreous chamber through which light passes to reach the retina, 9, from which the image is sensed by the optic nerve 10.

A variety of lens assemblies are available for implantation into the eye. Specific lenses have been designed for placement in the anterior chamber, 5, of the eye. Other lenses have been specifically designed for placement in the posterior chamber, 6, and still further lenses have been designed for attachment directly to the iris, 4.

Referring now to FIGS. 1A through 1C, there are shown three particular styles of intraocular lenses. All of these lenses have a light-refracting lens body, or optic 12 and support haptic loops 14 and 16 for supporting optic 12 in its proper location within the eye. All of these loops 14 and 16 are made of a soft, flexible filament usually made of a thermosetting, plastic polymer like polypropylene or polymethylmethacrylate, although a variety of other plastics and even metal loops may be used. The loops shown in FIG. 1A are called open loops because one end of each loop is attached to the optic and one end is free. The lens shown in FIG. 1B uses closed loops because both ends of the loops are attached to the optic. The lens shown in FIG. 1C has both a closed loop and an open loop. The lenses as shown in FIGS. 1A and 1C are principally used in the posterior chamber of the eye, whereas, the lens shown in FIG. 1B is principally used in the anterior chamber of the eye.

Intraocular Lens implantation can be an extremely difficult surgical procedure even for a very skilled surgeon. Inserting a lens like the lens shown in FIG. 1A into the posterior chamber, 6, of the eye requires very delicate and skillful manipulation. The lens must be inserted through an incision 18 (see FIG. 7a) made in the periphery of cornea 2, and a leading or inferior loop 14 must be inserted through the opening in the iris and against ciliary muscle 3. The body of the lens 12 and then the trailing or superior loop 16 is then inserted through the iris and released so the lens rests completely behind the iris. It is then sometimes necessary to position the lens properly.

An important feature of lens implant surgery is to minimize the size of the corneal incision so that it is just slightly larger than the size of the optic. A small incision reduces surgical trauma to the patient but requires more skillful manipulation by the surgeon. In some instances, it has been found useful to form an eyelet, 17, (see FIG. 1A) on a portion of the loop to facilitate the insertion and proper placement of the lens.

The lens shown in FIG. 1A can simplify the insertion process by reducing intraocular manipulations necessary by the surgeon. An intraocular lens with an optic diameter of about 6 millimeters is introduced into the anterior chamber 5 of the eye through a corneal incision 18 about 7 millimeters wide. The leading or inferior loop 14 is directed behind the inferior iris border, in front of the lens capsule and into the posterior chamber 6. See FIG. 7d. At this point, the surgeon may elect to proceed with conventional implant procedures if, for example, the eye is soft and favorable conditions exist. On the other hand, if positive vitreous pressure or patient restlessness is present, the surgeon may choose to suture the edges of incision 18, except for several millimeters, to permit subsequent entry of the trailing or superior loop 16 which has an eyelet 17 at its free end. A hook, 19, may then be inserted into eyelet 17 and superior loop 16 is placed into posterior chamber 6 by bending loop 16 inferiorly until the superior border of the iris is cleared. See FIG. 7c. The hook 19, may be hollow so that liquid may be introduced through it into the eye. While hook 19 is still in eyelet 17, pressure is then directed posteriorly toward optic nerve 10, compressing engaged loop 16 upon optic 12 until the implant is in posterior chamber 6. See FIG. 7d. Hook 19, still within eyelet 17, is slowly guided back toward the incision 18 decompressing superior loop 16 until the superior border of the iris is reached. See FIG. 7e. At this point, hook 19 is rotated (rather than lifted) out of eyelet 17 to prevent separating incision 18 during disengagement. See FIG. 7f. Superior loop 16 uncoils into position in the ciliary muscle 3 in the posterior chamber 6. See FIG. 7g. The surgeon has the option of either leaving the implant in the vertical orientation or rotating the implant so that it is oriented horizontally.

A major advantage of using eyelet 17 on a lens like that shown in FIG. 1A and the insertion technique that has just been described is that the entire implanting sequence can be accomplished with only one instrument. Iris retraction with a second instrument is unnecessary and, therefore, there is less intraocular manipulation, less incision separation and less chance of complication. The ability to further close the incision offers another advantage, as does the use of continuous irrigation of the operative site. Eyelet 17 will not snag the iris 4, and it gives the surgeon directional control of the intraocular lens in both the plane of the iris, as well as the anteroposterior plane perpendicular to the plane of the iris.

Eyelets may also be advantageously used to reduce the manipulations necessary during intraocular implantation surgery in lenses other than the open loop lens shown in FIG. 1A, for example, the closed loop lens shown in FIG. 1B and the combination of closed loop and open loop lens as shown in FIG. 1C.

In the past, various lens configurations have been found with eyelets in the haptic loops. For example, see U.S. Pat. No. 4,298,995 in which a haptic portion stamped from flexible plastic sheet material includes holes drilled or molded in various positions along the haptic. For soft plastic filamentary loop material like that used with the lenses shown in FIGS. 1A, 1B and 1C, the material is too thin to permit the molding or drilling of holes to form an eyelet. Consequently in the past, eyelets have been formed by overlapping the loop material and forming a bond at the overlapped portion by a heat-fusing process.

However, heat fusing can be a difficult and expensive process on a very thin filament of material like that used on the lenses in FIGS. 1A, 1B and 1C. First of all, the plastic form which the loops are made is primarily an insulating medium and can be quickly melted under the application of heat. Since the heat-fusing technique relies principally on conductive heat transfer through the insulating material, it can be difficult to form a good bond before the material completely melts.

In FIGS. 4 through 6, various heat-fusing techniques of the prior art are shown. In FIG. 4 a teflon-coated heat probe 50 is brought into contact to the side of the loop 51 in which an eyelet 53 is formed with a butt joint wherein the free end 52 of loop 51 is coiled back on itself to butt against the adjacent sidewall 54 of the remaining loop body 56. Loop 51 rests on platen 60. When probe 50 is energized, a portion of the material of loop 51 is melted by thermal conduction. The bond 58 is formed on the side of the loop closest to probe 50. Because the loop is an insulating material, heat takes a relatively long period of time to conduct through the loop material so that the bond area on the side of the loop opposite the probe 50 is less substantial than on the side of the loop adjacent the probe 50. (See FIG. 4.) In FIGS. 5 and 5a where free end 52 overlaps remaining loop body 56, the bonded area 58 tends to bulge. In FIGS. 6 and 6a where the free end 52 of loop 51 is cut at a bias and placed against the adjacent sidewall 54 of the remaining loop body 56, the bond 58 tends to have less material available to form the bond.

With a heat-fusing technique, the placement of the probe with respect to the area to be bonded is critical, partly because the material melts very quickly and partly because the material is generally insulated. Probe 50 is a thin needle with a diameter somewhat less than the diameter of the loop material. Placement of such a thin probe 50 with the precision that is necessary to form the weld is a difficult task. Using heat fusing, it is very difficult to get a smooth finish without excessive flash. Excessive flash would be undesirable, because the extra flash could irritate the very sensitive anatomy on the interior of the eye.

It is also important that the inside of eyelet 53 be generally circular and smooth so that there are no bumps or projections on which a surgical manipulating tool can catch. With the heat-fusing process, it is difficult to control the amount of excess material which can flow in to obstruct the circular interior of the eyelet, so that it is difficult to completely eliminate all rough surfaces and flash that could cause obstructions for a surgical tool.

It would be desirable to have a fast process which did not require precise placement of the loop but would still permit a strong smooth bond to be obtained to form the eyelet with a minimum of flash.

SUMMARY OF THE INVENTION

The present invention provides an intraocular lens loop with an eyelet, and a method for forming the eyelet, which addresses the problems encountered with heat fusing but which does not involve molding or drilling, so that the process can be used with a loop filament like those used with the lenses in FIGS. 1A, 1B and 1C. The loop of the present invention includes a body adapted for connection to an optic of an intraocular lens with an integral and continuous portion of that body disposed in overlapping relationship to define an eyelet with the confronting surfaces of the overlapped portion bonded together ultrasonically. The thermosetting plastic fiber material from which the loops shown in FIGS. 1A, 1B and 1C and the like are used is particularly well adapted for ultrasonic bonding.

In ultrasonic bonding of the present invention, the loop is formed in a desired shape with the portion of the loop material coiled in overlapping relationship to form an eyelet. At least the eyelet portion of the formed loop is placed on an anvil of an ultrasonic bonder. Then the eyelet overlapped portion is contacted by the horn of an ultrasonic bonder and compressed by the horn so that the thickness of the overlapped portion is not less than the thickness of the remaining body of the loop material. The horn is then energized so that a bond is formed in the overlapped portion.

In ultrasonic bonding, the mechanism of energy transfer is high-frequency vibration which develops frictional heating at the interface between the overlapped portions sufficient to at least partially melt the adjacent material to form a bond. The ultrasonic energy is then turned off, and the eyelet bond is allowed to cool before the horn is removed, so that a strong bond is formed. The eyelet may be placed at the end of an open loop or somewhere along the length of a closed loop.

The ultrasonic bonding is accomplished at ultrasonic frequencies with an amplitude of preferably between 12% and 25% of the height of the loop material, and most desirably about 16%. Although it is not critical, the ultrasound is applied for a time period preferably between 0.5 to 3 seconds, and most desirably approximately 0.75 seconds. The weld is then allowed to cool for a period of time before the horn is lifted and the loop is removed from the anvil. Although this time period is not critical, a cooling time of at least about 0.3 seconds is desirable.

The horn of the ultrasonic bonder is brought into contact with the overlapped portion of the loop and compresses the overlapped portion to a thickness not less than the thickness of the loop material in the non-overlapped region.

In a preferred embodiment of the present invention, a micrometer stop is placed on the structure that supports the horn so that the gap between the anvil and the horn is set at a height equal to the height of the loop material in the non-overlapped region. When the horn is brought into contact with the overlapped material, it continues to compress the overlapped region until the micrometer stop is contacted. The horn is pneumatically positioned, and when the pneumatic system senses the resistance of the horn structure against the micrometer stop, the horn energizes.

To further facilitate the manufacture of haptic loops, the loop material may be wrapped on a special fixture which includes a special base and a form. The exterior perimeter of the form defines the desired shape of the loop. Enough material to make ten (10) or more loops may be wrapped on the form in vertical coiled orientation. The loop material is wrapped round and round. The eyelet may be formed on each loop by coiling the loop material about a pin placed on the form. Clamps are provided for holding the loop material in position. The entire form, together with the associated loop material, is then baked in an oven at a desired temperature and then cooled under known conditions. This heating and cooling forms the loop material into the desired shape so that it will hold its shape after it is removed from the form. After cooling, the loop eyelets are trimmed, then the loops are cut to length, and each individual loop is removed from the form and subjected to the ultrasonic welding procedure.

Especially with eyelets formed at the end of open loops, it is important that the free end of the overlapping portion be trimmed flush with the adjacent sidewall of the overlapped portion, so that after welding the side surface of the loop will be smooth.

In order to obtain the desired quality and strength of bonding, it has been found that there is a desirable orientation of the overlapping portion with respect to the overlapped portion such that the axis of the free end of the overlapping portion intersects the sidewall of the overlapped portion at an angle alpha ($\alpha$) which is preferably between 90° and 160° and most preferably 150° (see FIG. 8). If angle alpha is 90°, the area of overlap will be the smallest and there is the least amount of material available to provide a strong bond. When the angle alpha is greater than about 160°, the area of overlap is large such that one tends to generate an undesirably large amount of flash and excess bonded material, so that the bond tends to have bulges, rough edges and may bulge into the interior of the eyelet so that projections may develop which can impede the smooth action of a positioning hook in the eyelet.

The loop with the ultrasonically bonded eyelet and the method for making the ultrasonic bond of the present invention provide a loop for an intraocular lens which can be made much faster than a comparable heat-fused eyelet loop principally because the insulating material of which the loop is made is a slow thermal conductor. The ultrasonic energy medium transmits energy directly to the interface so that the melting of the loop material occurs directly at the bond location. The precise location of the eyelet with respect to the heat probe for heat fusing is not required with ultrasonic bonding. Thus, the bonding process can progress much faster. It has also been found that the ultrasonically bonded eyelet is almost three times stronger than the heat-fused eyelet and that the periphery of the eyelet is smoother with less flash, bulges and other undesirable discontinuities in the loop material. Also the eyelet can be more readily formed into a circle with less projections and obstructions for the surgeon's manipulating instrument. The ultrasonic bonding also makes it possible to form, trim and cut multiple loops at the same time.

Other features and advantages of the present invention will become apparent from the following detailed description of the preferred embodiment taken in conjunction with the following drawings.

BRIEF DESCRIPTION OF THE DRAWINGS

FIGS. 7a–g show a schematic representation of the steps employed to insert an intraocular lens with eyelet loops of the present invention.

DETAILED DESCRIPTION OF THE PREFERRED EMBODIMENT

The present invention relates to a loop for an intraocular lens which includes an eyelet for receiving a manipulating instrument to facilitate insertion of the intraocular lens. The eyelet is bonded ultrasonically to form a strong eyelet which can withstand radial forces directed generally in the plane of the optic of an intraocular lens and forces directed generally perpendicular to the plane of the optic without separating. The present invention also involves the method of ultrasonically bonding the eyelet and a special fixture used during the manufacture of the loop to help form the eyelet.

Figure 1A:
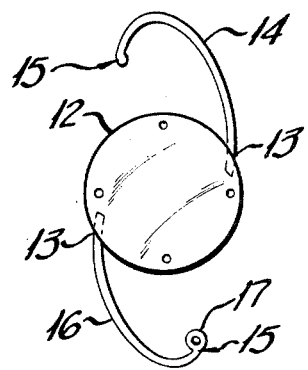
FIGS. 1A, 1B, and 1C show various intraocular lens configurations employing the eyelet loop of the present invention.
Figure 1B:
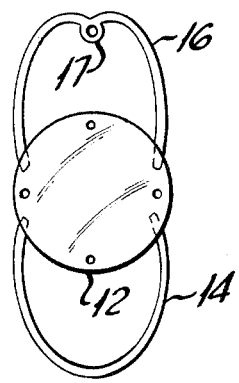
Figure 1C:
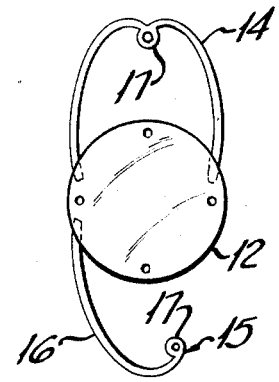

Referring now to FIGS. 1A, 1B and 1C, there are shown three types of intraocular lenses, all of which have a light-refracting lens body 12, commonly called an optic, and preferably made of a light, non-toxic, non-degradeable plastic like polymethylmethacrylate. Each of the optics has attached to it support loops 14 and 16, commonly called haptics, preferably made of a filament of thermosetting plastic polymer material like polypropylene. The haptic loops are preferably made of extruded filamentary material with a diameter of 4 to 8 mils. However, the diameter of the loop material is not critical, and any suitable diameter may be used. The loops also need not be circular in cross-section, and any convenient cross-sectional shape may be used. The kinds of materials from which the loops may be made include fiber-forming, thermosetting plastic polymers like polypropylene, polymethylmethacrylate, polyvinylidine fluoride, fiber-forming polyesters, fiber-forming nylons and fiber-forming fluoropolymers. This is only a short list of a large variety of materials that could be used. Metal loops have even been used in the past.

The lens shown in FIG. 1A has two open loops 14 and 16, one end 13 of each loop adapted for connection to optic 12 and the other end 15 of each loop is free. In the lens of FIG. 1A an eyelet 17 is formed on the free end 15 of haptic loop 16. Alternatively, the lens shown in FIG. 1B has two closed loops 14 and 16, both ends of which are adapted for attachment to optic 12. An eyelet 17 is placed at the mid-point of closed loop 16. However, eyelet 17 could be placed anywhere along the length of closed loop 16. In FIG. 1C, the optic 12 has a closed loop 14 and an open loop 16 with an eyelet 17 at free end 15 of open loop 16 and a second eyelet 17 at approximately the mid-point of closed loop 14. A wide variety of lens and loop geometries can employ the ultrasonically bonded eyelet of the present invention, and these lenses shown in FIGS. 1A, 1B and 1C are meant merely to show representative examples of suitable loop geometries.

Figure 2:
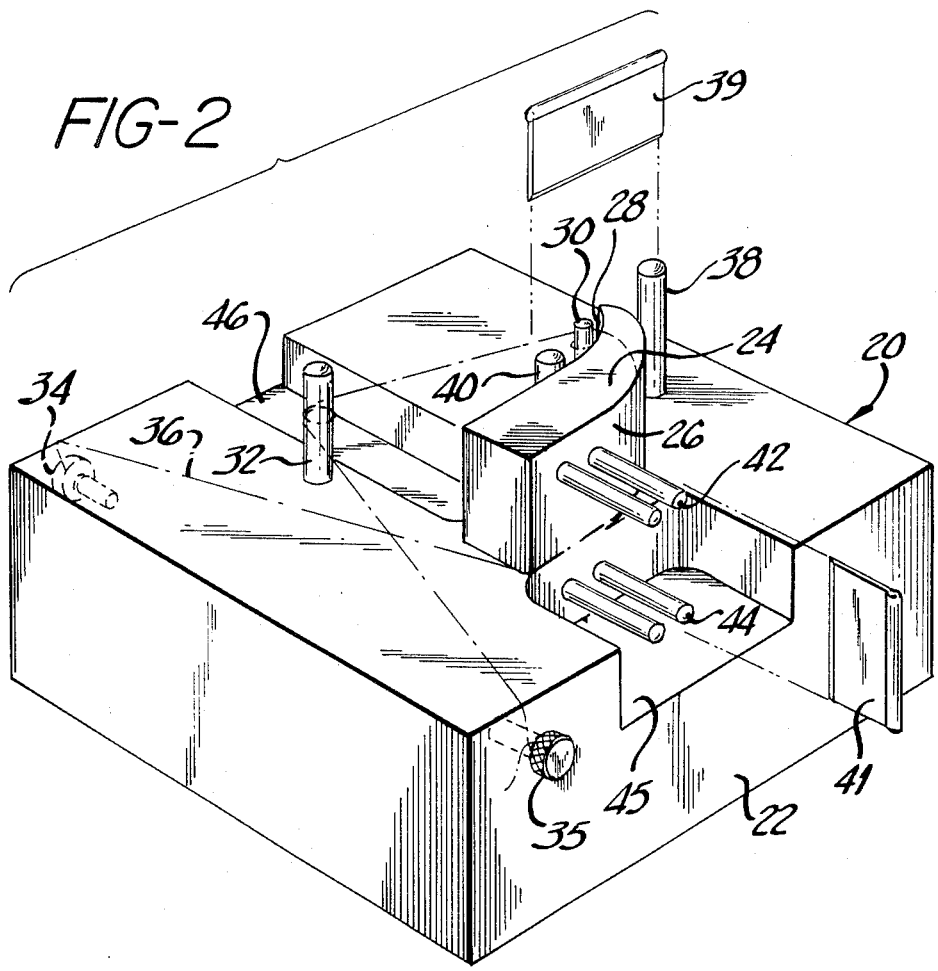
FIG. 2 shows a prospective view of a fixture used during the manufacturing process for eyelet loops of the present invention.
Figure 2A:
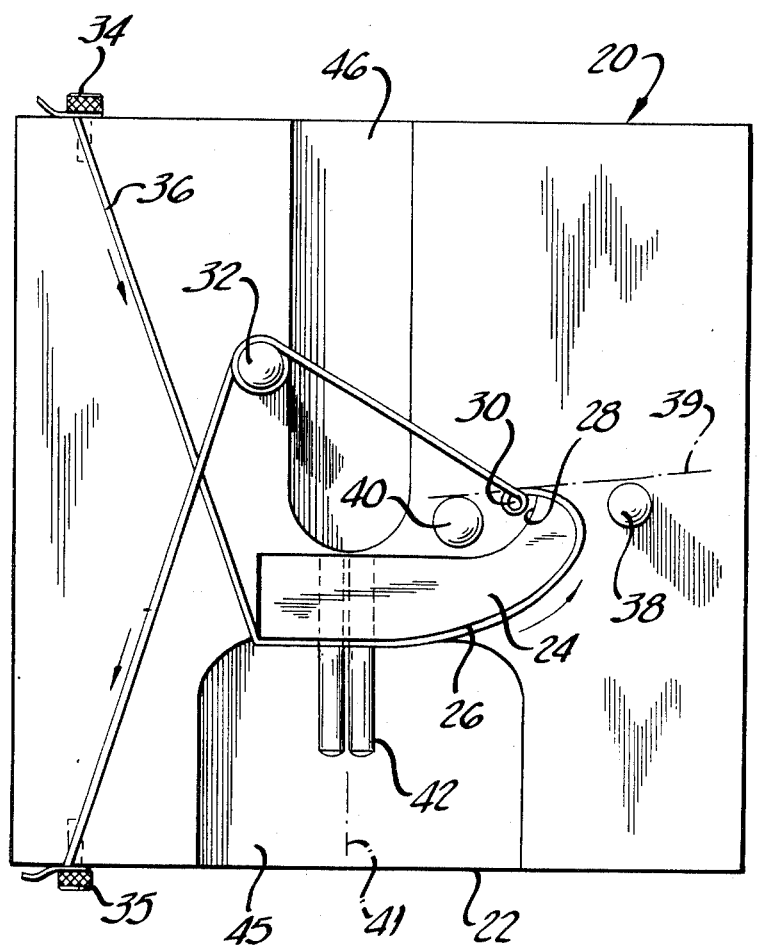
FIG. 2a shows a plan view of the fixture of FIG. 2.

Referring now to FIG. 2, there is shown a fixture specially designed to facilitate the manufacturing of a loop. Fixture 20 includes a base 22 and a form 24 projecting from base 22. The perimeter 26 of form 24 is shaped to conform to the desired loop configuration. Form 24 has a recess 28 within which an eyelet wrapping pin 30 is placed. A positioning pin 32 projects from base 22. Clamps 34 and 35 are provided on base 22. A quantity of loop material 36 is clamped into clamp 34 and wrapped loosely about the perimeter 26 of form 24, coiled about eyelet wrapping pin 30 to form an eyelet 17 and then wrapped around the surface of positioning pin 32 and clamped under clamp 35. As shown in FIG. 2A, loop material 36 is wrapped counterclockwise around pin 30 and extends over itself and then onto pin 32. This places the overlapped joint on the anterior side of the loop so that any flash or bulges will be less apt to irritate the anatomy of the eye. This forms one loop. Wrapping loop material around each of eyelet pins 30 and positioning pin 32 locks the material in place so that when one end of the loop is cut to size, the loop material does not release from the form.

Alternatively, a large number of loops may be formed simultaneously by wrapping loop material 36 around form 24 a number of times in a coiled configuration so that each coil is in contact with the perimeter 26 of form 24. Eyelets 17 are formed by wrapping loop material 36 about pin 30. As will be explained later in greater detail, the angle at which loop material 36 crosses over itself to form eyelet 17 is controlled by the location of positioning pin 32. After loop material 36 is wound onto form 24 and clamped in place on fixture 20 by means of clamps 34 and 35, the entire form is placed in an oven and baked at a desired temperature for a desired period of time to slightly shrink loop material 36 and to set the shape of loop material 36 to conform to the shape of the perimeter 26 of form 24, so that the loop will maintain that shape after the loops are cut to the correct length and removed from fixture 20. After loop material 36 is heated, it is cooled on the form for a desired period of time. Guide posts 38 and 40 are mounted on base 22 to provide guides for a cutter 39 to trim the free end of the eyelet flush to the adjacent sidewall of the body of the loop material. As will be explained later in the application, the angle of this cut is important and is determined by the location of positioning pin 32.

Two sets of additional guide posts 42 and 44 are provided to act as guides for a second cutter 41 to cut the loops to the proper length. The upper set of guide posts 42 are pins press fit into holes in form 24. These holes go all the way through form 24 so that if pins 42 break, they can be easily removed from the holes. Guide posts 44 are placed in recess 45 below the surface of base 22 and extend into holes in base 22. These holes extend through base 22 to a second recess 46 on the opposite side of form 24 so that if the pins which form guide posts 44 break, they may be easily removed from the holes. The two guide posts 42 are spaced closely together so that cutter 41 may fit closely between them to cut loop material 36 to the desired is length. The two guide posts 44 are similarly spaced. The guide posts 42 and 44 are aligned vertically so that cutter 41 will be aligned perpendicularly to loop material 36. Note that after the cut is made in the vicinity of the eyelet, loop material 36 still remains tight on form 24 because the eyelet loop wound-wrapping pin 30 remains relatively tight, and the wrap of loop material around positioning pin 32 locks loop material 36 on pin 32. Thus, when the first cut is made at the eyelet, the loop material in the vicinity of pins 42 and 44 is still tight to allow a good second cut to be made.

The multiple number of loops that are wound on the form 24 may be trimmed with one motion and then cut with one more motion, so that a significant amount of manufacturing time is saved. After the loops are cut, they are removed from the form and are ready for ultrasonic welding of the eyelet.

Figure 8:
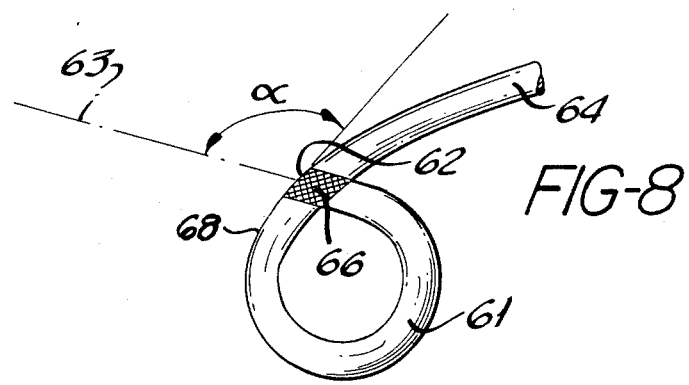
FIG. 8 shows a detail view of a bonded loop.
Figure 4:
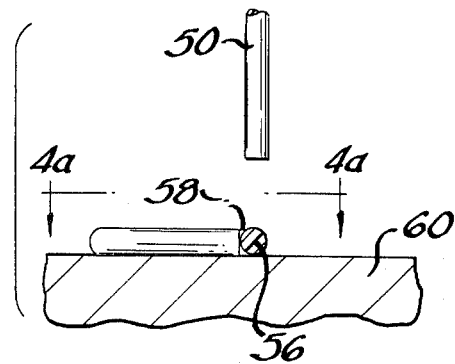
FIGS. 4 and 4a through 6 and 6a show various heat-fusing methods of the prior art.
Figure 4A:
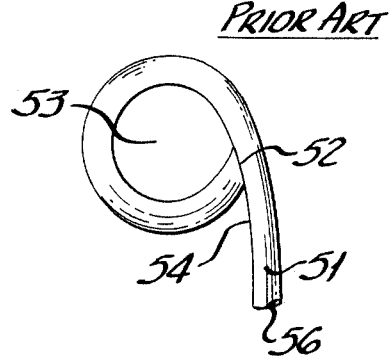
Figure 5:
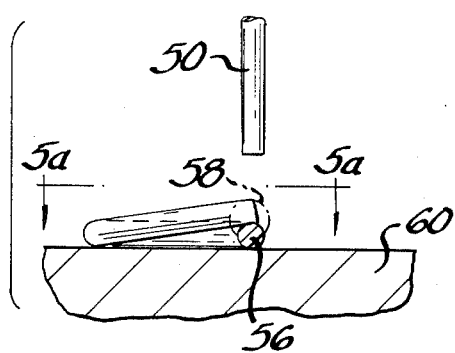
Figure 5A:
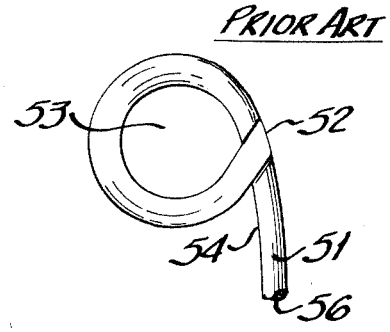
Figure 6:
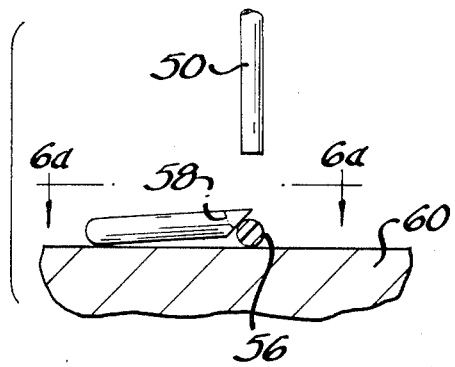
Figure 6A:
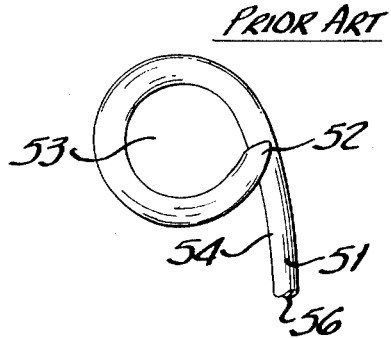

Referring now to FIG. 8, there is shown an enlarged view of the eyelet portion of the loop before the eyelet is bonded. Eyelet portion of the loop 61 is shown after it is removed from fixture 20 with the free end 62 of the eyelet portion overlapping the remaining body portion 64 of the loop. The quantity of material that is available to form the bond is shown in cross-hatching 66, and the angle defined by the longitudinal axis 63 at the free end 62 of eyelet 61 is shown forming an angle alpha ($\alpha$) with the tangent to adjacent sidewall 68 of the overlapped portion of loop body 64 at the point where axis 63 intersects sidewall 68. It will be appreciated by those skilled in the art that if angle alpha ($\alpha$) is ninety degrees (90°), the amount of material 66 available for bonding is at a minimum. If angle alpha is a larger obtuse angle, the amount of material available for bonding increases. I have found that there is a preferred angle alpha in the range of 90° to 160°, and most preferably about 150°, which provides the right amount of material for bonding but avoids excess material which could result in the formation of excess flash, bulges or protuberances which could effect the smoothness of the finished bond or which could create bumps or projections within the eyelet which could interfere with the smooth insertion of a manipulation instrument. The preferred angle is also chosen to make the shape of the interior perimeter of eyelet 61 substantially circular to further facilitate the easy insertion and withdrawal of a manipulation tool.

Figure 3:
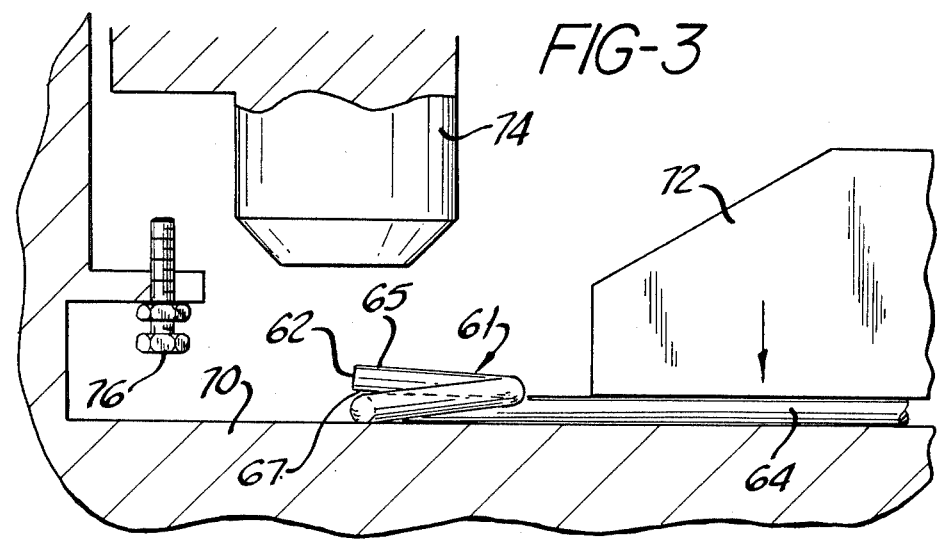
FIG. 3 shows a schematic elevational view of an ultrasonic bonding apparatus used in the present invention.
Figure 3A:
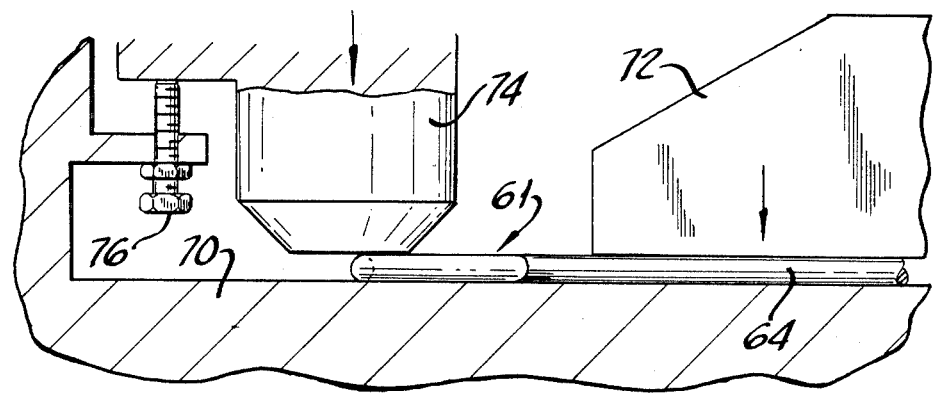
FIG. 3a shows the ultrasonic bonder of the present invention in position to bond an eyelet.

Referring now to FIG. 3, there is shown an ultrasonic bonding apparatus useful in performing the method of the present invention to form the ultrasonically bonded eyelet of the present invention. After a loop is formed and cut of fixture 20, and removed from fixture 20, at least the eyelet portion 61 of the loop is placed on base 70 of the ultrasonic welding apparatus. The remaining loop body 64 may be clamped onto base 70 by means of clamp 72. It is particularly apparent from FIG. 3 that the free end 62 of eyelet 61 overlaps the adjacent body portion 64 to form a height above base 70 equal to twice the diameter of the loop material in the body area 64. Ultrasonic horn 74 may be raised and lowered automatically by use of well known ultrasonic bonding control apparatus. Horn 74 is a solid metal piece which is caused to vibrate at ultrasonic frequencies at a desired amplitude. Horn 74 is lowered into contact with the upper surface 65 of free end 62 of eyelet 61. Free end 62 of eyelet 61 is then compressed as horn 74 is lowered further toward base 70. The amount which horn 74 drops toward base 70 is carefully controlled, so that the eyelet in the area to be bonded is not compressed to a thickness less than the thickness of the loop material in the uncompressed body portion 64 of the loop. A micrometer stop 76 may be used to carefully control the spacing between base 70 and horn 74 when horn 74 is compressed onto the overlapped region of the loop which is to be bonded. After the loop is clamped onto base 70, the ultrasonic bonder is activated, and horn 74 advances toward base 70 until the micrometer stop 76 is contacted. Horn 74 is positioned by a pneumatic cylinder. After micrometer stop 76 is contacted, the pneumatic system of the ultrasonic bonder senses that horn 74 has reached its ready position, and the bonder energizes automatically for a prescribed period of time which may be set by adjusting the appropriate controls on the bonder. The horn 74 vibrates vertically with a predetermined amplitude which may be adjusted, as will be described later in the application, by connecting boosters (not shown) to horn 74. These boosters adjust the amplitude of the ultrasonic vibration by using the particular geometry of the booster in a fashion which is well known to those skilled in the ultrasonic arts and, hence, will not be described further in this application.

The vertical vibrations of horn 74 transmit sonic waves through the loop material, which cause a frictional rubbing at the interface 67 of the overlapping section of the free end 62 of the loop and the overlapped portion of the loop body 64. This frictional movement causes heat to be generated at interface 67, which will at least partially melt the material of the loop. After the horn has been energized for a prescribed period of time, the ultrasound is de-energized but the horn is left in position compressing the overlapping loop onto the overlapped portion of the loop body for a further prescribed period of time so that the material in the area to be bonded 66, which has been at least partially melted by the ultrasonic energy, will have time to solidify to form a strong bond. Horn 74 is then lifted out of position, and the loop is unclamped from base 70. Another loop is placed on base 70 and the cycle is repeated.

Using this method of ultrasonic bonding, one achieves an eyelet 61 whose internal perimeter is almost completely circular. The bonded area is smooth and without flash, and there are no bulges or protuberances from the bond area and particularly no bulges or protuberances protruding into the interior perimeter of the eyelet. No additional finishing is needed to remove bulges, flash or protuberances from the bonded area.

This method of forming an eyelet on the loop of an intraocular lens is significantly faster than the heat fusing process described earlier in the application partially because the ultrasonic bonding does not require the precise placement of the eyelet with respect to a heat probe. The manufacturing procedure is further expedited by the use of the fixture of the present invention which permits several loops to be shaped and readied for ultrasonic bonding at one time.

The following are examples of the process carried out on specific loop materials. A loop of PROLENE* polypropylene suture material having a diameter of 6 mils was formed on a fixture 20 to the shape of the loop shown in FIG. 1A with an eyelet 17 formed on the free end of the loop. The formed loop with the overlapped eyelet was then clamped onto base 70 of an ultrasonic bonding machine known as a Branson No. 8144, which developed ultrasonic energy at a frequency of approximately 40,000 hertz. Ultrasonic frequencies are generally understood to be frequencies above 20,000 hertz. Frequencies in the range from 20,000 to 50,000 have been used but a frequency of 40,000 has most often been used. Frequencies somewhat below the generally accepted ultrasonic threshold of 20,000 hertz down to the area of 15,000 to 20,000 hertz are believed to be able to provide bonding, but I prefer to use frequencies in the range of 40,000 hertz. A horn having an end diameter of ¼" and an ultrasonic booster ratio of 1 to 1 was used. The horn was made of titanium. The micrometer stop 76 was adjusted so that the gap between the horn 74 and base 70 was 6 mils or 0.006 inches when the horn was fully compressed against the region of the overlapped eyelet which was to be bonded. The horn 74 was adjusted so that when the horn was in the raised position, its distance above the anvil was 1/32" or about 30 mils.
*Trademark of Ethicon, Inc.

The bonding time during which the horn was ultrasonically energized was 0.75 seconds, although this time period does not seem to be critical and a time period ranging from 0.5 to 3 seconds also provides satisfactory bonds.

The hold time during which the horn was held on top of the bonded area after the ultrasonic horn was de-energized was 0.3 seconds, although a longer period of time could be used to achieve a satisfactory result. Clamp 72 need not be used. In its place a pair of tweezers may be used to hold body portion 64 of the loop in its correct orientation on base 70 under horn 74.

The amplitude of vibration of the horn and its relationship to the thickness of the loop material seems to be critical. In this example, an amplitude of vibration of 1 mil for a 6 mil diameter PROLENE loop was used. The amplitude was adjusted using a 1 to 0.7 booster for the horn to reduce the amplitude of vibration and a 1 to 1.5 booster was also used to increase the amplitude of vibration. It was found that although the bonds with the 0.7 and 1.5 booster were satisfactory, the bonds were not as good as the bonds with the 1 to 1 booster used to achieve the 1 mil vibration amplitude. It was found that a ratio between vibration amplitude and loop diameter of between 12% and 25% worked satisfactorily but the most preferable ratio is between 15% and 17%. The criticality of this ratio makes it important to hold the horn at the right distance above the base 70. The micrometer stop 76 should be set at the diameter of the loop material so that the horn may compress the overlapped region of the eyelet which is to be bonded down to a thickness which is equal to one loop diameter.

The eyelets in the PROLENE loops formed in this test were subjected to quality assurance testing. A hook was placed in the eyelet and the loop body was clamped into position. The hook was pulled in a direction which would tend to expand the loop to its full radial dimension. A pull of 50 grams was exerted before the bond separated. Previous tests run on heat fused PROLENE loops made from the same diameter of the same loop material and configured in the same shape loop resulted in the bond breaking at a pull force of 17 gram. Force was also exerted in the direction perpendicular to the plane of the optic, and it was found that although the exact amount of grams force exerted was not measured that the eyelet was capable of sustaining force in that transverse direction. The area of the bond was smooth without bulges and without any flash, and the interior periphery of the eyelet was substantially circular without any protuberances or bulges which would interfere with the insertion or removal of the hook.

Those skilled in the art will appreciate that the present invention provides a strongly bonded eyelet for the loop of an intraocular lens which provides a smoothly continuous surface without bulges, flash or protuberances and which provides a fast and efficient method of manufacturing the eyelet. The present invention has been described in conjunction with the preferred embodiment. Those skilled in the art will appreciate that many modifications and changes may be made to the preferred embodiment without departing from the present invention. It is, therefore, not intended to limit the present invention except as set forth in the appended claims.

I claim:

1. A method of forming an eyelet on a haptic loop of an intraocular lens comprising the steps of:
   (a) forming loop material into a desired shape with a portion of said material coiled in overlapping relationship providing an overlapping portion and an overlapped portion of said loop to form an eyelet wherein the confronting surfaces of the overlapped loop material define an overlapped region for providing a bonding site;

(b) placing at least said overlapped region of said loop on an anvil of an ultrasonic bonder;

(c) contacting at least said overlapped region with the horn of an ultrasonic bonder;

(d) compressing the overlapped region with the horn of an ultrasonic bonder so that the resulting thickness of the compressed overlapped region is not less than the thickness of the loop material in the region of said loop that is not overlapped; and, (e) energizing the ultrasonic bonder to bond the confronting surface of the overlapped region.

2. The method of claim 1 wherein the step of forming includes:

placing loop material into a desired shape with a portion of said material coiled in overlapping relationship to form said eyelet;

clamping said loop material into position to hold said shape;

setting said loop material to maintain said shape when said clamping is released; and, cutting said formed loop to the desired length.

3. The method of claim 1 further including the step of stopping said horn a predetermined distance above said anvil and bringing said ultrasonic horn into contact with said overlapped region to compress said eyelet overlapped region.

4. The method of claim 2 wherein said setting step includes the steps of baking the loop material at a predetermined temperature for a predetermined period of time and then cooling said loop.

5. The method of claim 1 further including the step of clamping the loop material onto said anvil.

6. The method of claim 1 wherein said loop material includes a fiber-forming, therosetting plastic.

7. The method of claim 1 wherein the loop material includes a polymer.

8. The method of claim 1 wherein the loop material is made of any ultrasonically weldable metal.

9. The method of claim 1 wherein the loop material comprises polymethylmethacrylate.

10. The method of claim 1 wherein the loop material comprises polypropylene.

11. The method of claim 1 wherein the loop material comprises polyvinylidine fluoride.

12. The method of claim 1 wherein the loop material is a fiber-forming polyester.

13. The method of claim 1 wherein the loop material is a fiber-forming nylon.

14. The method of claim 1 wherein the loop material is a fiber-forming fluoropolymer.

15. The method of claim 6 wherein the amplitude of said ultrasonic vibration is in the range of about 12%–25% of the thickness of the loop material in the non-overlapped region.

16. The method of claim 15 wherein the ultrasonic horn is energized to a frequency in the range of approximately 18,000 hertz to 50,000 hertz.

17. The method of claim 1 wherein said loop is an open loop and wherein said eyelet is formed at the free end of said open loop.

18. The method of claim 1 wherein said eyelet is substantially circular.

19. The method of claim 17 wherein said forming step includes trimming the free end of said overlapping portion of said eyelet flush with the adjacent sidewall of the overlapped portion of said loop material.

20. The method of claim 19 wherein said overlapping eyelet is cut at a bias angle alpha formed between the longitudinal axis of the overlapping portion and the tangent to the adjacent sidewall of the overlapped portion at the point where said axis intersects said adjacent sidewall, said angle being in the range of 90° to 160°.

21. A method of forming an eyelet on a haptic loop of an intraocular lens, said loop having a body portion and an eyelet portion comprising the steps of:

(a) coiling a portion of said loop material in overlapping relationship to the adjacent body portion to provide an overlapping portion and an overlapped portion of said loop to form an eyelet wherein the confronting surfaces of the overlapped loop material define an overlapped region for providing a bonding site;

(b) placing said body of said loop in a desired shape;

(c) holding said loop material into position to hold its shape;

(d) forming said loop material to maintain said shape when said holding is released;

(e) trimming and cutting said formed loop to a desired length;

(f) placing said eyelet portion in at least said overlapped regions of said cut loop on an anvil of an ultrasonic bonder;

(g) contacting said eyelet portion in at least said overlapped region with the horn of an ultrasonic bonder;

(h) compressing said eyelet portion in at least said overlapped region with said horn so that the resulting thickness of the compressed overlapped region is not less than the thickness of the adjacent body portion of the loop; and, (i) energizing said ultrasonic bonder to provide a bond at said bonding site.

22. The method of claim 21 wherein the overlapping edge of said eyelet portion is trimmed flush with the adjacent sidewall of said body portion of loop material which is overlapped so that the cut surface forms a bias angle and the longitudinal axis of the overlapping portion of between 90° and 160°.

23. The method of claim 21 wherein the coiling and placing steps are reversed.

24. The method of claim 6 wherein the energizing step is carried out for a period of 0.5 to 3 seconds; and, further including the steps of deenergizing the ultrasonic bonder, leaving the ultrasonic horn in contact with the said overlapped region and permitting said bonded eyelet to cool for a predetermined period of time.

25. The method of claim 24 wherein said cooling step lasts for at least 0.3 seconds.

26. A fixture for use in forming an eyelet on a haptic loop of an intraocular lens comprising:

a base;

a form mounted on said base a part of the perimeter of said form defining the desired shape of said loop;

a first projection extending from said base about which said loop material may be wrapped in overlapping relationship to provide an overlapping portion and an overlapped portion of said loop to form an eyelet;

positioning means extending from said base and positioned with respect to said first projection and said form to determine the angle at which said overlapping portion crosses said overlapped portion of said eyelet;

first guide means on said fixture to facilitate cutting said loop material to a desired length.

27. The fixture of claim 26 further including second guide means operatively disposed on said fixture and adapted to facilitate the trimming of an eyelet placed at the free end of an open loop whereby said overlapping portion of the eyelet may be trimmed flush with the adjacent sidewall of said overlapped portion.

28. The fixture of claim 26 wherein said first guide means include
   a recess in the surface of said base on which said form is mounted;
   at least one guide post extending from said base into said recess, at least one guide post extending from said form aligned with said base recess guide post to cooperatively provide a guide for a cutting edge.

29. The fixture of claim 28 further including a second recess in said base aligned with said first recess to provide access to facilitate removal of said base recess guide posts.

30. The fixture of claim 27 wherein said second guide means includes a pair of projections mounted on said base.

31. A haptic loop for an intraocular lens comprising:
   a body adapted for connection to the optic of an intraocular lens;
   an integral and continuous portion of said body disposed in overlapping relationship to define an eyelet portion of the loop material;
   the confronting surfaces of said overlapped region bonded together ultrasonically;
   wherein said ultrasonically bonded area of said loop is substantially continuous with said adjacent body, and the transition area from said body to said bonded area is substantially smooth and is substantially without excess material.

32. The loop of claim 31 wherein the body includes a fiber of thermosetting plastic.

33. The loop of claim 32 wherein said thermosetting plastic is selected from the group of polymethylmethacrylate, polypropylene, polyvinylidine fluoride, fiber-forming polyesters, fiber-forming nylons or fiber-forming fluoropolymers.

34. The loop of claim 31 wherein
   said loop is an open loop having a first end adapted for connection to the optic of an intraocular lens and a free end; and,
   said eyelet is formed at the free end of said loop.

35. The loop of claim 31 wherein
   said loop is a closed loop with first and second ends both adapted for connection to the optic of an intraocular lens; and,
   said eyelet is formed at a position between said first and second ends along the body of said loop.

36. The loop of claim 31 wherein said eyelet is disposed in the plane of said body.

37. The loop of claim 31 wherein the internal perimeter of said eyelet is substantially circular.

38. A haptic loop for an intraocular lens comprising:
   a body adapted for connection to the optic of an intraocular lens;
   an integral and continuous portion of said body disposed in overlapping relationship to define an eyelet portion of the loop material;
   the confronting surfaces of said overlapped region bonded together ultrasonically;
   wherein said confronting surfaces of the overlapping loop material define an overlapped region to provide a bonding site which is bonded ultrasonically by:
   placing at least said eyelet region of said loop on an anvil of an ultrasonic bonder;
   contacting at least said overlapped region with the horn of an ultrasonic bonder;
   compressing said overlapped region with said horn so that the resulting thickness of the compressed overlapped region is not less than the thickness of said loop body; and,
   then energizing the ultrasonic bonder for a predetermined period of time.

39. The loop of claim 38 wherein said ultrasonic bonding is carried out at an amplitude of ultrasonic vibrations in the range of about 12% to 25% of the thickness of the loop material in the nonoverlapped region.

* * * * *